(12) United States Patent
Kawasaki et al.

(10) Patent No.: US 11,786,118 B2
(45) Date of Patent: Oct. 17, 2023

(54) IMAGE DISPLAY DEVICE AND IMAGE DISPLAY SYSTEM

(71) Applicant: NIKON CORPORATION, Tokyo (JP)

(72) Inventors: Tomohiro Kawasaki, Yokohama (JP); Masahiro Mizuta, Yokohama (JP); Ryoichi Sataka, Yokohama (JP); Toshiyuki Namikawa, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 553 days.

(21) Appl. No.: 16/823,833

(22) Filed: Mar. 19, 2020

(65) Prior Publication Data

US 2020/0214562 A1    Jul. 9, 2020

Related U.S. Application Data

(63) Continuation of application No. PCT/JP2018/034919, filed on Sep. 20, 2018.

(30) Foreign Application Priority Data

Sep. 22, 2017 (JP) .................................. 2017-182460
Apr. 11, 2018 (JP) .................................. 2018-076377

(51) Int. Cl.
*A61B 3/103* (2006.01)
*A61B 3/00* (2006.01)
(Continued)

(52) U.S. Cl.
CPC .............. *A61B 3/103* (2013.01); *A61B 3/005* (2013.01); *A61B 3/13* (2013.01); *A61B 3/14* (2013.01)

(58) Field of Classification Search
CPC ........ G02B 2027/0138; G02B 27/0172; G02B 5/30; G02B 27/0081; G02B 27/283; G02B 27/144; G02B 27/145; G02B 27/0093; G02B 5/3083; G02B 2027/011; G02B 13/0055; G02B 17/0856; G02B 27/0068;
(Continued)

(56) References Cited

U.S. PATENT DOCUMENTS

2018/0284470 A1    10/2018    Yamamoto et al.

FOREIGN PATENT DOCUMENTS

| JP | 2000-214388 | * | 1/1999 | ............. G02B 21/22 |
| JP | 2000-214388 A | | 1/2000 | |
| JP | 2009-288696 | | 12/2009 | |

OTHER PUBLICATIONS

International Search Report dated Nov. 13, 2018 in corresponding International Application No. PCT/JP2018/034919.

(Continued)

*Primary Examiner* — Brandi N Thomas

(57) ABSTRACT

In an ophthalmic imaging system an image imaged by an imaging section for a right eye is formed as an imaging image on a display, and then displayed through a right-eye optical unit and a reflection member. An image imaged by an imaging section for a left eye is formed as an imaging image on a display, and then displayed through an optical unit and the reflection member. This thereby enables the object to be visually inspected as a three-dimensional image by the observer viewing the right-eye imaging image and the left-eye imaging image, which differ from each other according to the parallax therebetween, by viewing the respective images through right and left eyes.

19 Claims, 15 Drawing Sheets

(51) Int. Cl.
*A61B 3/13* (2006.01)
*A61B 3/14* (2006.01)

(58) Field of Classification Search
CPC ............. G02B 17/0896; G02B 27/286; G02B 5/3066; G02B 17/0804; G02B 2027/013; G02B 27/0905; G02B 27/0983; G02B 27/148; G02B 5/3041; G02B 5/305; G02B 5/3058; G02B 2027/0118; G02B 27/0101; G02B 2027/0123; G02B 27/0176; G02B 1/10; G02B 2027/0194; G02B 27/28; G02B 21/04; G02B 2027/0134; G02B 2027/015; G02B 2027/0178; G02B 6/00; G02B 2027/0125; G02B 27/1066; G02B 21/361; G02B 2027/0132; G02B 2027/0136; G02B 27/1073; G02B 6/003; G02B 6/0031; G02B 6/0055; G02B 6/0056; G02B 6/105; G02B 2027/014; G02B 21/10; G02B 27/14; G02B 21/22; G02B 17/08; G02B 2027/0174; G02B 21/0012; G02B 25/001; G02B 2027/0187; G02B 21/367; G02B 5/1833; G02B 5/1861; G02B 2006/0098; G02B 2027/0185; G02B 27/1006; G02B 3/00; G02B 30/36; G02B 5/1809; G02B 5/1847; G02B 5/3016; G02B 17/0816; G02B 2027/0127; G02B 2027/0141; G02B 2027/0154; G02B 2027/0169; G02B 21/002; G02B 21/368; G02B 25/008; G02B 27/027; G02B 30/35; G02B 2027/0147; G02B 21/16; G02B 21/365; G02B 26/0825; G02B 27/0179; G02B 30/26; G02B 13/0045; G02B 13/006; G02B 13/0065; G02B 13/009; G02B 13/22; G02B 30/34; G02B 5/04; G02B 13/007; G02B 13/0075; G02B 17/0621; G02B 17/0808; G02B 2027/0181; G02B 21/18; G02B 26/06; G02B 27/01; G02B 27/0149; G02B 30/24; G02B 30/56; G02B 5/32; G02B 6/10; G02B 13/00; G02B 17/0832; G02B 17/0848; G02B 17/086; G02B 2027/0116; G02B 21/025; G02B 21/084; G02B 21/362; G02B 21/364; G02B 23/2415; G02B 27/00; G02B 27/48; G02B 5/005; G02B 7/021; G02B 15/144105; G02B 21/0032; G02B 21/004; G02B 21/0088; G02B 21/06; G02B 21/241; G02B 21/244; G02B 21/245; G02B 21/34; G02B 26/106; G02B 27/017; G02B 30/25; G02B 30/52; G02B 30/54; G02B 5/10; G02B 7/10; G02B 7/183; G02B 15/144113; G02B 15/144511; G02B 15/145511; G02B 19/0066; G02B 21/00224; G02B 21/0028; G02B 21/0048; G02B 21/0072; G02B 21/0084; G02B 21/24; G02B 26/0833; G02B 26/10; G02B 27/0043; G02B 27/0075; G02B 27/02; G02B 27/025; G02B 27/08; G02B 27/642; G02B 3/08; G02B 5/0273; G02B 5/18; G02B 5/201; G02B 5/26; G02B 6/0026; G02B 6/005; G02B 7/023; G02B 7/08; G02B 7/102; G02B 7/12; A61B 5/0059; A61B 2562/0238; A61B 3/1233; A61B 5/0062; A61B 5/05; A61B 5/14546; A61B 8/06; A61B 5/48; A61B 90/20; A61B 1/00193; A61B 90/37; A61B 2090/371; A61B 3/132; A61B 2090/373; A61B 2017/00207; A61B 2017/00216; A61B 2034/2048; A61B 2090/365; A61B 2090/372; A61B 2090/502; A61B 3/10; A61B 90/25; A61B 90/361; A61B 3/0008; A61B 3/0041; A61B 3/1025; A61B 3/113; A61B 5/0077; A61B 5/06; A61B 5/1171; A61B 5/1176; A61B 5/339; A61B 5/4803; A61B 1/0005; A61B 2034/2055; A61B 3/0091; A61B 3/107; A61B 5/24; A61B 1/00048; A61B 1/00194; A61B 2017/00973; A61B 2090/306; A61B 2090/309; A61B 2090/3933; A61B 2090/3941; A61B 2576/00; A61B 3/102; A61B 3/1225; A61B 3/13; A61B 3/14; A61B 34/20; A61B 5/1455; A61B 90/50; A61B 2090/364; A61B 2560/0487; A61B 3/0025; A61B 3/09; A61B 3/1015; A61B 3/135; A61B 1/00009; A61B 1/00039; A61B 1/0004; A61B 1/00042; A61B 1/00149; A61B 1/045; A61B 1/051; A61B 1/24; A61B 3/0066; A61B 3/18; A61B 2562/0233; A61B 3/1005; A61B 5/0036; A61B 5/4836; G03B 21/28; G03B 17/00; G03B 21/14; G03B 35/18; G03B 35/24; G03B 21/006; G03B 21/208
See application file for complete search history.

(56) References Cited

OTHER PUBLICATIONS

Written Opinion of the International Searching Authority dated Nov. 13, 2018 in corresponding International Application No. PCT/JP2018/034919.

\* cited by examiner

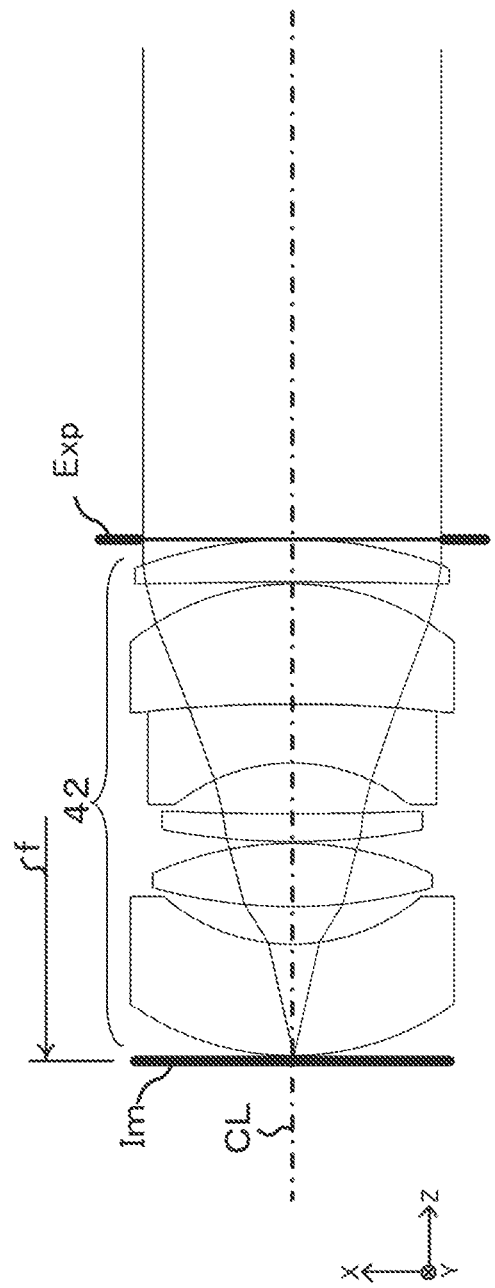

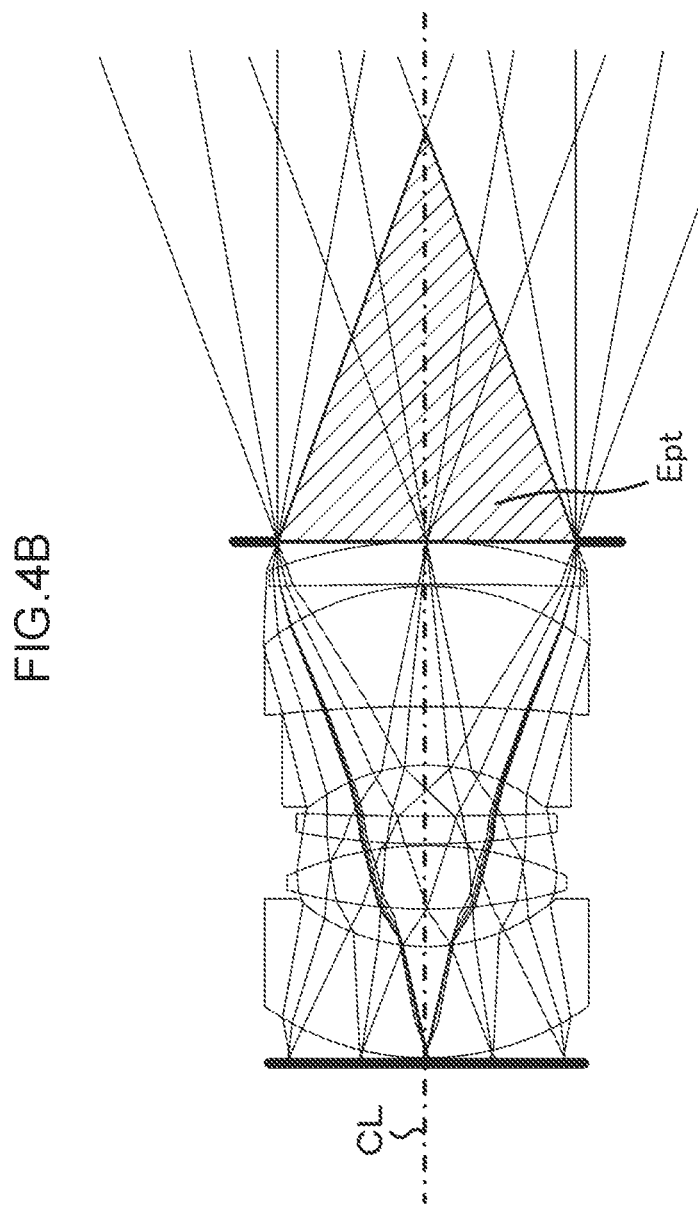

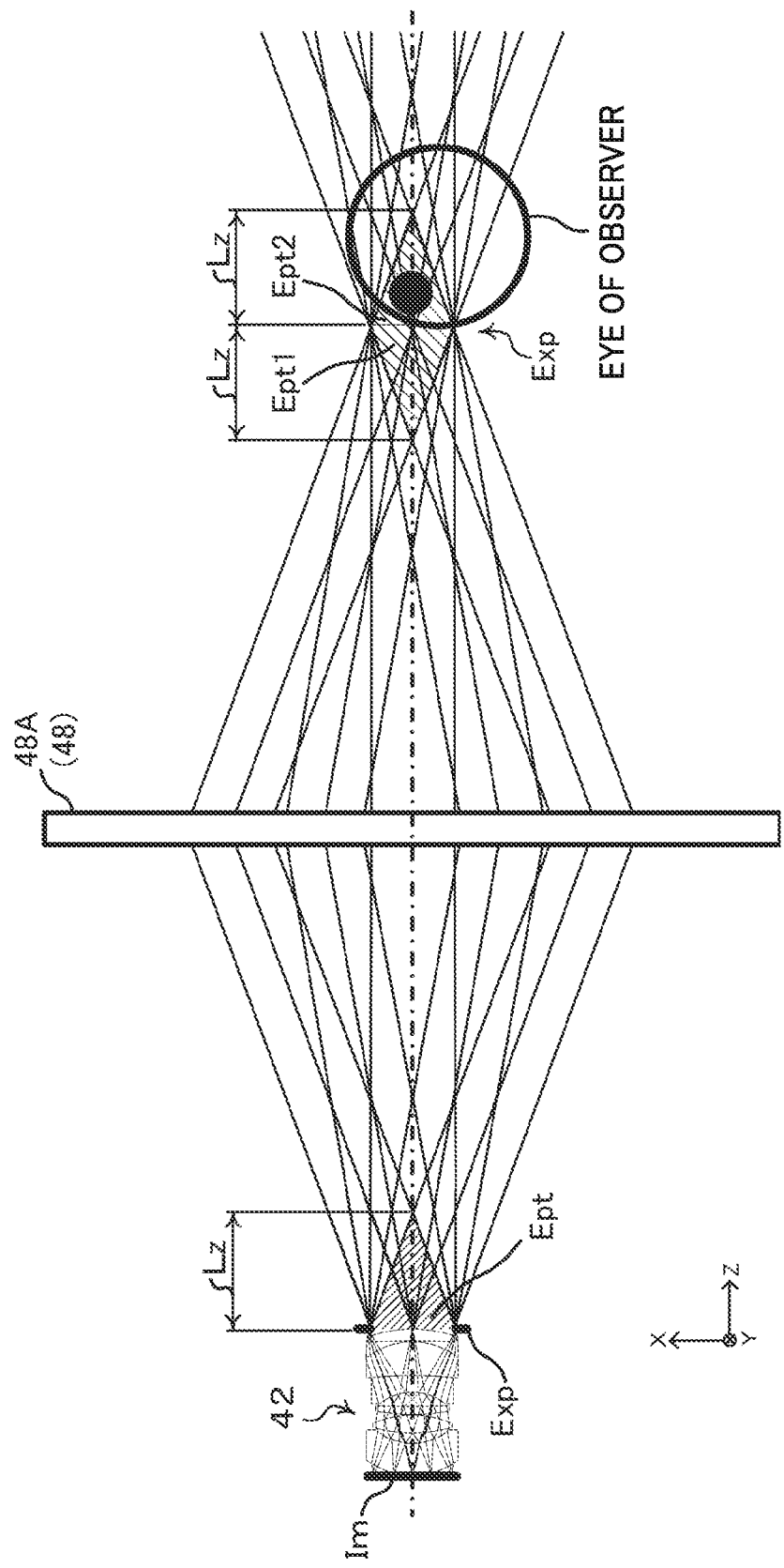

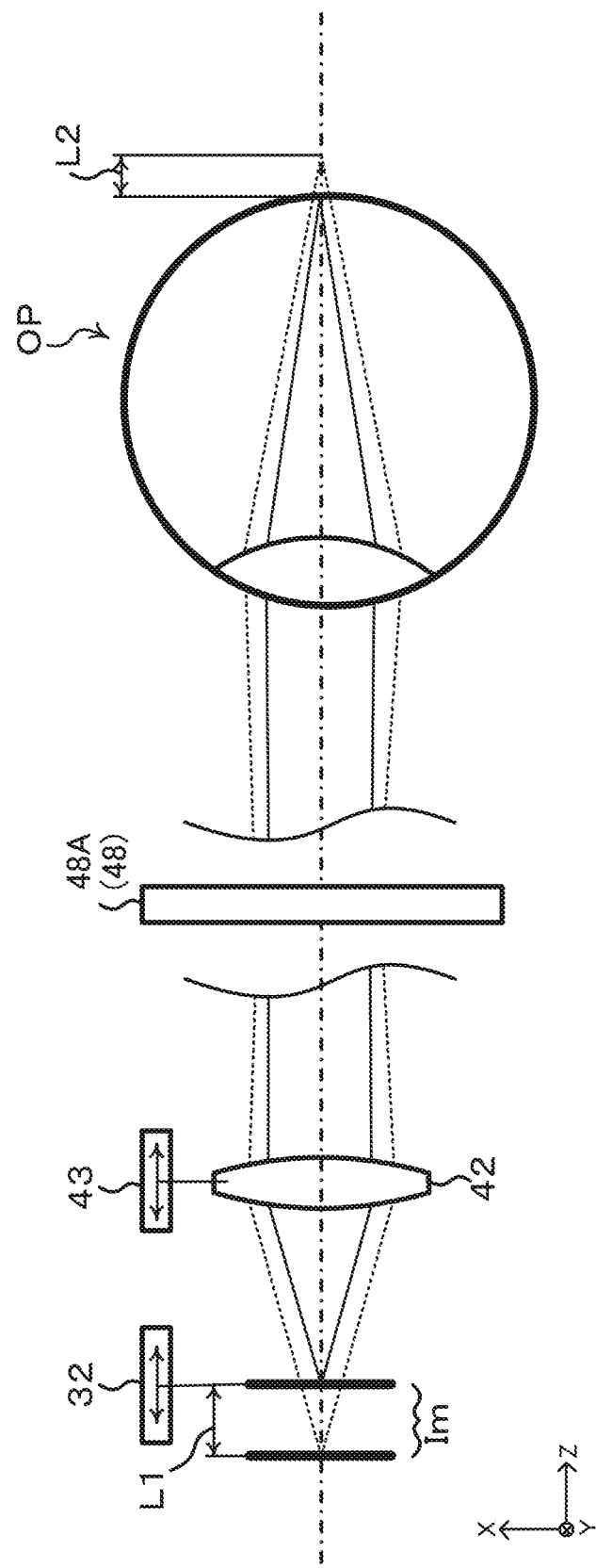

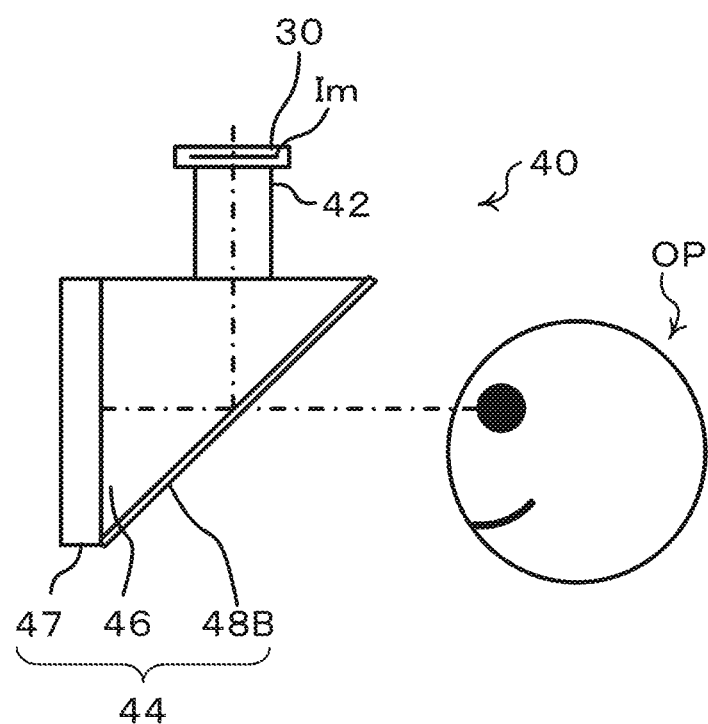

IMAGE DISPLAY DEVICE AND IMAGE DISPLAY SYSTEM

CROSS-REFERENCE TO RELATED APPLICATION

This application is a continuation application of International Application No. PCT/JP2018/034919, filed Sep. 20, 2018, the disclosure of which is incorporated herein by reference in its entirety. Further, this application claims priority from Japanese Patent Application No. 2017-182460, filed Sep. 22, 2017 and Japanese Patent Application No. 2018-076377, filed Apr. 11, 2018, the disclosure of which is incorporated herein by reference in its entirety.

TECHNICAL FIELD

Technology disclosed herein relates to an image display device and an image display system.

BACKGROUND ART

In ophthalmology there are various implementations of ophthalmic imaging devices capable of observing the eyes of subjects (hereafter referred to as subject eyes) for the purpose of ophthalmic diagnostics and surgical treatment of the eyes. Moreover, recently ophthalmic imaging devices capable of observing a subject eye with binocular vision have also been implemented. In the present specification "ophthalmology" refers to the medical field for treating eyes. Technology related to image display devices capable of observing objects such as a subject eye with binocular vision is also known (see Patent Document 1).

In the technology described in Patent Document 1, a virtual image is formed for a real image projected by a projector using a reflection element that includes functionality to perform spatial replication twice on incident light, as an optical system that does not require a screen.

RELATED ART

Patent Literature

Patent Document 1: Japanese Patent Application Laid-Open (JP-A) No. 2009-288696.

SUMMARY OF INVENTION

An aspect of technology disclosed herein is an image display device including an optical unit that has a focal point on an incident side of light at a position where an image of an object is set, and that is configured to form an exit pupil, and an optical element configured to reflect or pass light emitted from the optical unit and relay the exit pupil to a position having a conjugate relationship to the exit pupil.

BRIEF DESCRIPTION OF DRAWINGS

FIGS. 4A and 4B are sketches illustrating an example of optical paths of an optical unit in an ophthalmic imaging system according to an exemplary embodiment.

FIG. 5 is a sketch illustrating an example of optical paths of a display device included in an ophthalmic imaging system according to an exemplary embodiment.

FIG. 9 is a schematic diagram illustrating an example of a diopter adjustment mechanism to adjust diopters to match the eyes of an observer, according to an exemplary embodiment.

FIG. 11 is a block diagram illustrating a first modified example related to a display device in an ophthalmic imaging system according to an exemplary embodiment.

DESCRIPTION OF EMBODIMENTS

Figure 1:
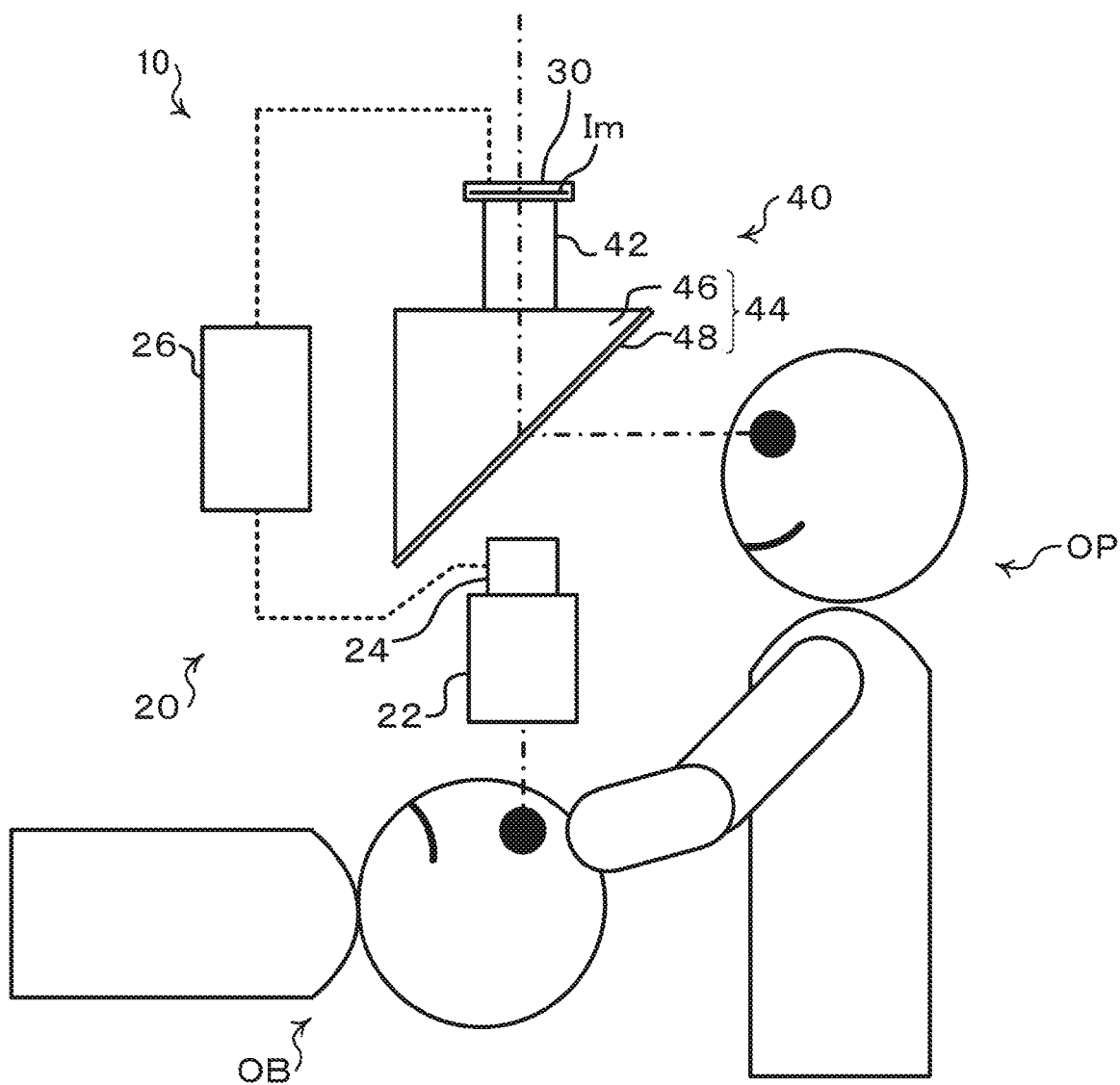
FIG. 1 is a block diagram illustrating an example of an overall configuration of an ophthalmic imaging system according to an exemplary embodiment.

Explanation follows regarding exemplary embodiments, with reference to the drawings.

In the technology disclosed herein, an image display device according to technology disclosed herein is applicable to any device for displaying images, and an image display system according to technology disclosed herein is applicable to any system equipped with a device for displaying images. In the present exemplary embodiment, for ease of explanation, as an example of an image display system according to technology disclosed herein, a case will be described of an ophthalmic imaging system applied with an ophthalmic imaging device, for an observer such as a doctor to observe an eye (subject eye) of a patient or the like and the periphery of the subject eye for the purpose of ophthalmic diagnostics and surgical treatment of the eyes in ophthalmology.

Although an example of an image display system according to technology disclosed herein will be described for an ophthalmic imaging system applied with an ophthalmic imaging device, the image display system according to technology disclosed herein is not limited to an ophthalmic imaging system applied with an ophthalmic imaging device. Namely, there is no limitation to an image display device to display an image imaged by an imaging device employed in ophthalmology to image a subject eye and a periphery of the subject eye, and application may be made to any image display device and image display system in which an object is imaged, without limitation to ophthalmology, and the imaged image is displayed. For example, in medical fields, application may be made to image display devices and image display systems employed in any field of medicine. Moreover, the image display system according to technology disclosed herein is not limited to an image display device or image display system employed in any medical field, and is obviously applicable to any image display device and image display system capable of displaying images.

Moreover, although a description follows in the present exemplary embodiment of a case in which an image imaged by an imaging device of a subject eye and the periphery of the subject eye is employed as an imaged image and the imaged image is displayed, as an example of a case in which the technology disclosed herein is applied, the imaged image may be a still image, and may also be a video image. Moreover, the image employed in the present exemplary embodiment is not limited to an imaged image. Namely, employing an image imaged by an imaging device as the imaged image is merely an example of technology disclosed herein. For example, the technology disclosed herein is also applicable to an image display device and an image display system for displaying pre-prepared images.

In the present exemplary embodiment, as an example of an image display system according to technology disclosed herein, an example will be described of an ophthalmic surgical microscope employed when an observer such as a doctor operates while observing the subject eye and the periphery of the subject eye of a patient or the like as an example of application to an ophthalmic imaging system. The application in this case to an ophthalmic surgical microscope is also merely an example of an image display system according to technology disclosed herein, and in medical fields, application may be made to surgical microscopes employed in any field of medicine. The image display system according to the technology disclosed herein is also not limited to a surgical microscope employed in a medical field, and obviously application may be made to another optical device including a microscope for observing objects.

FIG. 1 illustrates an example of a configuration of an ophthalmic imaging system 10 according to the present exemplary embodiment.

As illustrated in FIG. 1, the ophthalmic imaging system 10 includes an imaging section 20 to image the subject eye and periphery of the subject eye as an object OB, a display section 30, such as a display, to display the image imaged with the imaging section 20, and a display device 40 used to display to an observer OP the imaged image of the display section 30. In the ophthalmic imaging system 10, the subject eye and the periphery of the subject eye of the observation subject is imaged by the imaging section 20, the image imaged thereby is formed in the display section 30, and the imaged image is displayed for the observer OP using the display device 40.

The display section 30 such as a display is detachably attached to the display device 40 so as to form the display section 30-equipped display device 40. Namely, the ophthalmic imaging system 10 according to an exemplary embodiment of the present is a system formed from the imaging section 20 and independent display section 30-equipped display device 40, enabling separate movement of the imaging section 20, and separate movement of the display section 30-equipped display device 40. Moreover, as discussed in more detail below, an overall device that includes the display section 30-equipped display device 40, a case serving as a housing section to house the display device, and a stand to which these are fixed, is installed at a position distanced away from the observer OP and arranged so as to be in a non-contact state with respect to the head of the observer OP.

The ophthalmic imaging system 10 according to the present exemplary embodiment will be described with reference to an example of a case in which the observer OP views (with binocular vision) the eye (subject eye) and the periphery of the subject eye that are the object OB using both eyes of the observer OP. Namely, the ophthalmic imaging system 10 independently forms an optical path of an image to be displayed for the right eye of the observer OP, and an optical path of an image to be displayed for the left eye of the observer OP. More specifically, the imaging section 20 includes a right-eye imaging section 20R and a left-eye imaging section 20L, the display section 30 includes a right-eye display section 30R and a left-eye display section 30L, and the display device 40 includes a right-eye display device 40R and a left-eye display device 40L. Note that in the following description the suffixes R and L will be omitted unless there is a need to discriminate between use with the right eye or the left eye.

In the following description, an eye width direction between the eyes of the observer OP when the ophthalmic imaging system 10 is installed in a horizontal plane is referred to as the "Y direction", a direction perpendicular to the horizontal plane is referred to as the "X direction", and a direction of light toward the observer OP when an image of the object OB is viewed by the observer OP is referred to as the "Z direction".

The imaging section 20 is equipped with a microscope 22, a camera 24, and a camera controller 26. The microscope 22 is an optical system to observe the object OB, i.e. the subject eye and the periphery of the subject eye. Note that since the same configuration is employed in the imaging section 20 for the right eye and for the left eye, separate explanation thereof will be omitted. The camera 24 is an electronic device for converting images produced by the microscope 22 of the object OB, i.e. the subject eye and the periphery of the subject eye, into a picture signal. The camera controller 26 is an electronic device for converting the picture signal into a display signal. The camera controller 26 is connected to the display section 30, a typical example thereof being a liquid crystal monitor or the like, and outputs a display signal to the display section 30. The image imaged by the camera 24 is thereby formed as an imaging image Im on the display section 30. Note that since the same configuration is employed in the display section 30 for the right eye and for the left eye, separate explanation thereof will be omitted. The observer OP operates the microscope 22, and sets the microscope 22 at an observation position to observe the object OB, i.e. the subject eye and the periphery of the subject eye.

The display device 40 is equipped with an optical unit 42 and a reflection section 44. The optical unit 42 is an example of an optical unit of technology disclosed herein, and functions as an objective lens to refract at least light from the incident imaging image Im and to emit the refracted light (described in detail later). The reflection section 44 includes a case 46 and a reflection member 48. The display device 40 is attached to a stand, omitted from illustration, is independently formed from the imaging section 20, and is formed so as to be in a non-contact state with respect to the observer OP. Forming the display device 40 so as to be in a non-contact state with respect to the observer OP suppresses the observer OP from feeling unsettled by contact occurring of the observer OP with the display device 40.

In the ophthalmic imaging system 10 according to the present exemplary embodiment, the imaging section 20, and the display section 30-equipped display device 40, are independently formed from each other, enabling separate respective movements thereof. Thus, even in cases in which the imaging section 20 has been moved to change the observation position while the observer OP is viewing the object OB (for example the subject eye and the periphery of the subject eye) using the display device 40, the display device does not move, and so the observer OP is able to view the imaging image Im without head movement. This is advantageous for operation in cases such as those in which an ophthalmic surgical microscope is applied as the imaging section 20. For example, in cases in which operating is being performed while moving the operating field, the observer OP such as a doctor is able to concentrate on operating while viewing the operating field without changing viewing position. Moreover, due to being able to form the imaging section 20 and the display section 30-equipped display device 40 independently from each other, as long as the imaging section 20 is able to image the object OB, the degrees of freedom are increased for the shape of the imaging section itself.

Figure 2A:
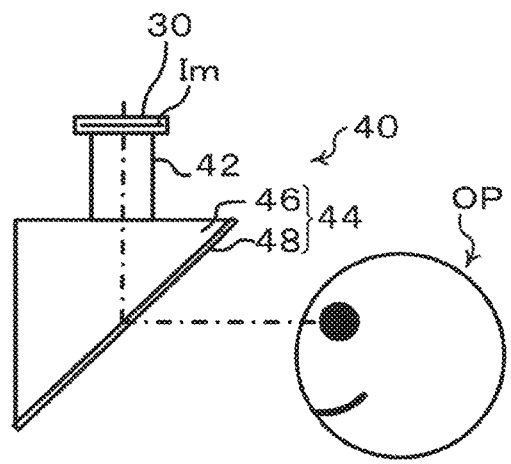
FIGS. 2A to 2C are sketches illustrating an example of a configuration of a display device in an ophthalmic imaging system according to an exemplary embodiment.
Figure 2B:
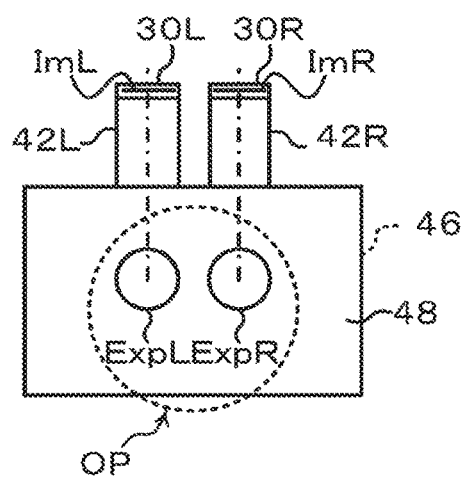
Figure 2C:
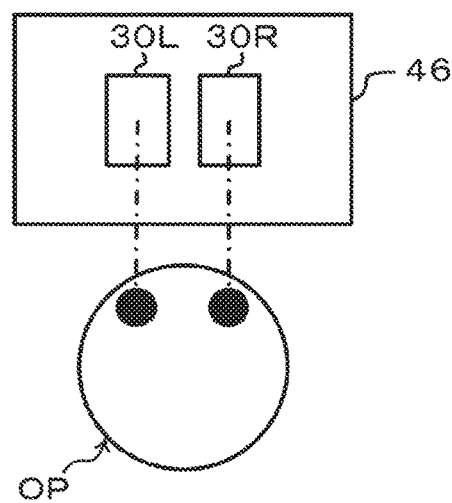

FIGS. 2A to 2C illustrate an example of a configuration of the display device 40. FIG. 2A illustrates a side view of the display device 40, FIG. 2B illustrates a front view, and FIG. 2C illustrates a plan view from above. Note that the example illustrated in FIGS. 2A to 2C is an example in which the reflection section 44 is a common reflection section employed for both the right eye and the left eye.

As illustrated in FIGS. 2A to 2C, in the display device 40, the right-eye display device 40R displays an imaging image ImR formed by the display section 30R (of an image from the imaging section 20R) for the right eye of the observer OP through the right-eye optical unit 42R and the reflection member 48. The left-eye display device 40L displays an imaging image ImL formed by the display section 30L (of an image from the imaging section 20L) for the left eye of the observer OP through the left-eye optical unit 42L and the reflection member 48.

As illustrated in FIG. 2B, the display device 40 forms a right-eye exit pupil ExpR and a left-eye exit pupil ExpL at the light exit side of the display device 40, namely, in front of the observer OP (described in detail later). In the following description, the right-eye exit pupil ExpR and the left-eye exit pupil ExpL will be referred to collectively as "exit pupil Exp" unless there is a need to distinguish between left and right.

The ophthalmic imaging system 10 of the present exemplary embodiment accordingly forms the image imaged by the right-eye imaging section 20R on the display section 30R as the imaging image ImR, and then displays this image through the optical unit 42R and the reflection member 48. Moreover, the image imaged by the left-eye imaging section 20L is formed on the display section 30L as the imaging image ImL, and then this image is displayed through the optical unit 42L and the reflection member 48. This thereby enables the object OB to be visually inspected as a three-dimensional image by the observer OP viewing the right-eye imaging image ImR and the left-eye imaging image ImL, which differ from each other according to the parallax therebetween, by viewing the respective images through right and left eyes.

Figure 3:
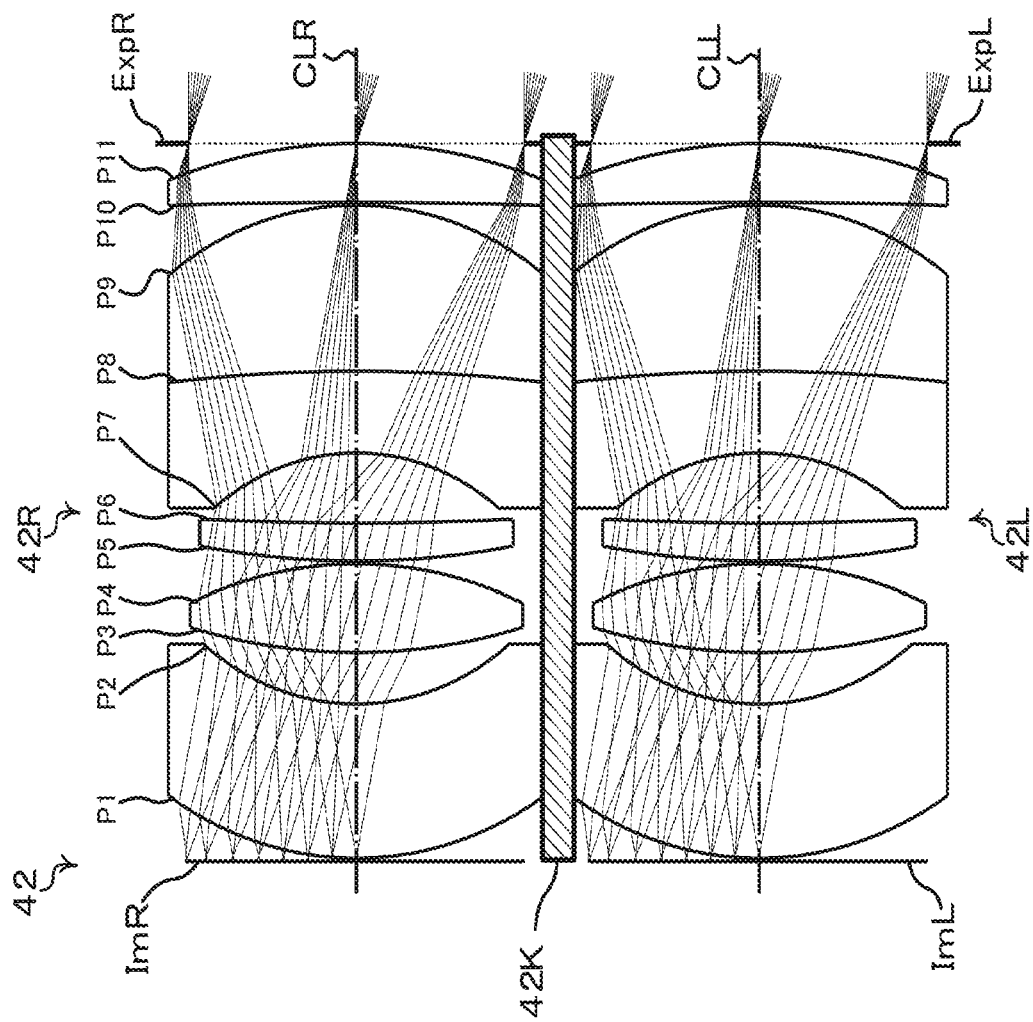
FIG. 3 is a sketch illustrating an example of a configuration of an optical unit in an ophthalmic imaging system according to an exemplary embodiment.

FIG. 3 illustrates an example of a configuration of the optical unit 42 including the optical unit 42R and the optical unit 42L.

As illustrated in FIG. 3, the optical unit 42R forms a lens system equipped with optical surfaces of Surface Nos. P1, P2, P3, P4, P5, P6, P7, P8, P9, P10, and P11, in this sequence from the imaging image ImR. The optical surfaces are refraction surfaces where the refractive index of the transmission medium on one side of the optical surface boundary is different from the refractive index of the transmission medium on the other side thereof.

Specification values of the optical unit 42R are listed in the following Table 1.

In Table 1, Surface No. m corresponds to the Surface Nos. of the optical surfaces illustrated in FIG. 3. The radius of curvature r indicates a radius of curvature for each of the optical surfaces, the inter-plane distance d indicates a distance along the optical axis from one of the optical surfaces to the next optical surface, the refractive index nd indicates a refractive index with respect to D-lines, and dispersion vd indicates an Abbe number thereof. Although in the specification listed in Table 1 the units of "mm" are adopted for the radius of curvature r and for the inter-plane distance d, equivalent optical properties are obtained by proportional enlargements or proportional shrinking of the optical unit 42R, and so there is no limitation to units of "mm", and another unit may be employed.

TABLE 1

| Surface No. m | Radius of Curvature r (mm) | Inter-Plane Distance d (mm) | Refractive Index nd | Dispersion vd |
|---|---|---|---|---|
| P1 | −59.236 | 0.5 | | |
| P2 | −41.97 | 24 | 1.84666 | 23.8 |
| P3 | −108.212 | 8.04 | | |
| P4 | 70.804 | 13.71 | 1.7725 | 49.6 |
| P5 | −159.548 | 0.43 | | |
| P6 | −592.485 | 5.92 | 1.7725 | 49.6 |
| P7 | 39.499 | 10.9 | | |
| P8 | 300.567 | 12.75 | 1.84666 | 23.8 |
| P9 | 53.951 | 25.85 | 1.618 | 63.3 |
| P10 | 1082.29 | 0.43 | | |
| P11 | 95.127 | 9.16 | 1.7725 | 49.6 |

Note that Table 1 relates to an example in which the optical surfaces have spherical shaped faces with an axis along the optical axis CLR; however, the optical surfaces are not limited to being spherical shaped faces, and may be non-spherical shaped faces.

The optical unit 42L is configured similarly to the optical unit 42R, and so detailed explanation thereof will be omitted.

In the present exemplary embodiment, a light suppressing section 42K is provided between adjacent optical units, namely, between the optical unit 42R and the optical unit 42L. The light suppressing section 42K functions as a partitioning section to suppress extraneous light from one of the optical unit 42R or the optical unit 42L entering the other thereof. The light suppressing section 42K may be configured in any manner that enables light from one of the optical unit 42R or the optical unit 42L to be suppressed from entering the other thereof, and is more preferably capable of blocking light. The light suppressing section 42K preferably includes a light absorbing material. By including a light absorbing material, the light suppressing section 42K not only suppresses light from one of the optical unit 42R or the optical unit 42L entering the other thereof, but also suppresses light reflection.

The end portions of the optical unit 42R and the optical unit 42L, for example the edge faces thereof, contact the light suppressing section 42K. Contacting the optical unit 42R and the optical unit 42L with the light suppressing section 42K keeps the gap between the optical unit 42 and the light suppressing section 42K to a minimum, and sets each crosswise length of the optical unit 42R and the optical unit 42L to substantially the length of the diameter of the optical unit 42.

In this manner, the optical unit 42 includes the optical unit 42R and the optical unit 42L, enabling the imaging image Im to be viewed with both eyes of the observer OP. The optical unit 42R and the optical unit 42L have similar configurations to each other, so separate description thereof will be omitted, and they will be referred to in general as optical unit 42. The optical unit 42 functions as an objective lens to emit light from the imaging image Im as light of an afocal system. Namely, the optical unit 42 has a focal length f, and the display section 30 is attached to the optical unit 42 such that the imaging image Im of the object formed by the display section 30 is set at the position of the focal point on the light incident side.

FIGS. 4A and 4B illustrate an example of an optical path of the optical unit 42. FIG. 4A illustrates an optical path of light propagating in a direction along the optical axis CL, and FIG. 4B illustrates optical paths including peripheral optical paths.

As illustrated in FIG. 4A and 4B, the optical unit 42 is set such that the imaging image Im of the object formed by the display section 30 is positioned at the focal point position of the focal length f on the display section 30 side. Light emitted from the optical unit 42 is thereby light of an afocal system, namely, parallel light. The parallel light emitted from the optical unit 42 reaches the eyes of the observer OP through the display device 40, described in detail later, and forms an image on the retinas of the observer OP, and the imaging image Im is sensed by the observer OP.

The light emitted from the optical unit 42 is emitted toward the observer OP through the display device. However, this light is parallel light, and so the apparent size, namely the size of the imaging image Im viewed by the observer OP, does not change. In other words, the optical unit 42 emits parallel light so that the size of the imaging image Im does not change. By forming the optical unit 42 so as to emit parallel light in this manner, the apparent size does not change. What this means is, for example, that the size of an image does not change even if the distance between the reflection section 44 and the eyes of the observer OP changes.

By configuring the optical unit 42 such that the apparent size does not change, even if the observer OP were to change position in either a direction approaching the display device 40 or a direction away from the display device 40, for example, even if the head of the observer OP was to move forward or aft along the optical axis direction, the observed size of the imaging image Im would not change. The observer OP is thereby permitted to undertake a larger change in posture than in a case in which there is a set posture to view the imaging image Im according to the size of the imaging image Im.

However, the optical unit 42 is preferably formed such that the first surface on which light is incident (the optical surface of Surface No. P1 illustrated in FIG. 3) is a refraction surface configured by a convex face on the light incident side. The optical unit 42 suppresses attenuation of peripheral light by bringing most rays of light close to parallel to the optical axis. Fluctuations in magnification when defocused are also suppressed.

Moreover, in order to correct chromatic aberration, preferably at least one or more doublet lens is included in the optical unit 42. Furthermore, in such a doublet lens configured by a convex lens and a concave lens, preferably the Abbe number of the convex lens is greater than that of the concave lens. In the optical unit 42 of the present exemplary embodiment, the doublet lens is positioned in a lens group formed by the optical surfaces of Surface Nos. P7, P8, P9 illustrated in FIG. 3; however, the position is not important, and chromatic aberration may be corrected as long as one of the lenses is a doublet lens.

Moreover, the optical unit 42 is formed such that the exit pupil Exp is positioned at a position at or beyond the outermost surface on the light exit side of the optical unit 42. Cases in which the exit pupil Exp is positioned at a position at or beyond the outermost surface on the light exit side of the optical unit 42 are cases in which the optical unit 42 is suppressed from becoming more bulky. An example of a configuration of the optical unit 42 is a configuration in which the exit pupil Exp is positioned at a position at or beyond the last lens as light is emitted from the optical unit 42, for example, the lens forming the optical surfaces of Surface Nos. P10 and P11 illustrated in FIG. 3. A configuration may also be adopted in which the exit pupil Exp is positioned at a position at or beyond a nearest lens to the reflection section 44 that is positioned at the light exit side from the optical unit 42.

The optical unit 42 according to the present exemplary embodiment is an example of a case in which the exit pupil Exp is positioned at the outermost surface on the light exit side of the optical unit 42 (on a flat plane orthogonal to the optical axis CL and including the point of intersection between the optical surface of Surface No. P11 and the optical axis CL). However, the position of the exit pupil is not limited to being at the outermost surface on the light exit side of the optical unit 42, and the optical unit 42 is suppressed from becoming more bulky even in cases in which the exit pupil is positioned in the vicinity of the outermost surface.

An example of the optical unit 42 formed such that the position of the exit pupil Exp is positioned at or beyond the outermost surface on the light exit side is a configuration in which the outermost surface of the optical unit 42 is a concave face. Namely, the refraction surface furthest to the display section 30 side (the first refraction surface of technology disclosed herein) is formed so as to be a convex face on the display section 30 side, and the refraction surface positioned furthest to the light exit side (the second refraction surface of technology disclosed herein) is formed so as to be a convex face on the display section 30 side. For example, as illustrated in FIG. 3, the optical surface of Surface No. P1 is the refraction surface furthest to the display section 30 side (the first refraction surface of technology disclosed herein), and the optical surface of Surface No. P11 is the refraction surface positioned furthest to the light exit side (the second refraction surface of technology disclosed herein). Note that the outermost surface of the optical unit 42 is not limited to being formed as a concave face, and appropriate modifications may be implemented according to the optical design of the optical unit 42.

In this manner, by forming the optical unit 42 such that the exit pupil Exp is positioned at a position at or beyond the outermost surface on the light exit side, the exit pupil of the optical unit 42 can be formed with a size corresponding to the lens diameter of the optical unit 42. Moreover, forming the exit pupil of the optical unit 42 at a size corresponding to the lens diameter of the optical unit 42 is equivalent to providing an aperture of a size corresponding to the lens diameter of the optical unit 42. In other words, by configuring the position of the exit pupil Exp at a position at or beyond the outermost surface on the light exit side of the optical unit 42, the exit pupil Exp is formed with the same size as the lens diameter of the lens that includes the outermost surface, for example, the lens formed with the optical surfaces of Surface Nos. P10 and P11 illustrated in FIG. 3.

When the observer OP is viewing with both eyes so as to view with binocular vision or the like, preferably the left and right images are displayed at a separation from each other corresponding to the pupil distance (PD) between the two eyes of the observer OP. Thus, the lens diameter in the optical units 42R, 42L is preferably not greater than the pupil distance PD. For example, taking an observer with a pupil distance PD of 65 mm as the standard, the lens diameter in the optical units 42R, 42L is preferably not greater than 65 mm.

The optical unit 42 is also preferably formed according to the following design conditions.

A first design condition is that the optical unit 42 is formed with a focal length not greater than 100 mm so as to satisfy the following conditional equation:

$$f \leq (D/2)/\sin \theta$$

wherein f is the focal length of the optical unit 42, D is a size of imaging image Im formed by the display section 30, and θ is a light illumination half angle of view of light with respect to the optical axis of the optical unit 42.

The length D of the imaging image Im is preferably set to a length not less than the shortest straight line out of straight lines on the imaging image Im that pass through the center of the imaging image Im. For example, in cases in which the imaging image Im is circular in shape, then the diameter is taken as length D. Moreover, in cases in which the imaging image Im is elliptical in shape, then the minor axis is taken as length D. Note that the center of the imaging image Im may be the optical axis, may be a gaze axis as viewed by the observer, or may be any position within the imaging image Im.

By employing the first design condition, the optical unit 42 can be formed considering a constraint to the size of the imaging image Im formed by the display section 30, and a constraint to the light illumination angle of view with respect to the optical axis of the optical unit 42. For example, in cases in which a length of the imaging image Im is not greater than a standard predetermined 65 mm employed for the pupil distance PD for binocular viewing, and in which the illumination angle of view θ is equivalent to or greater than that of a standard eyepiece lens for a field number 18 at a magnification of 10×, then the focal length f is not less than 100 mm.

A second design condition is that the optical unit 42 is formed with a focal length of not less than 25 mm so as satisfy the following conditional equation:

$$f \geq S/\tan R$$

wherein f is the focal length of the optical unit 42, S is the size (pixel size) of pixels configuring the imaging image Im formed by the display section 30, and R is an eye resolving power.

By employing the second design condition, the optical unit 42 can be formed considering a constraint of the size of pixels configuring the imaging image Im formed by the display section 30, and a constraint of the eye resolving power. Namely, a reduction in quality of the imaging image Im arising from sensing the size of the pixels configuring the imaging image Im by utilizing the eye resolving power can be suppressed from occurring. For example, taking the size of pixels configuring the imaging image Im formed by the display section 30 (pixel size) S to be 15 μm or greater, then in cases in which the eye resolving power R is 2 minutes of arc, the focal length f is not less than 25 mm.

From the first design condition and the second design condition, in cases in which the pupil distance PD of the observer OP is 65 mm and the pixel size S for forming the imaging image Im by the display section 30 is 15 μm or greater, then the focal length f of the optical unit 42 is preferably from 25 mm to 100 mm.

As illustrated in FIG. 1 and FIG. 2, the reflection section 44 includes the case 46 and the reflection member 48. The optical unit 42 is attached to the case 46, and the light that has been emitted from the optical unit 42 is introduced into the case 46. Moreover, the reflection member 48 is attached at the inside of the case 46 at the light exit side of the optical unit 42, so as to reflect light along a direction intersecting with the emitting optical axis of the optical unit 42 (i.e. in a direction toward the observer OP). The reflection section 44 reflects the light that has been emitted from the optical unit 42 along the direction intersecting with the emitting optical axis of the optical unit 42, and forms an exit pupil at a position on the reflection side having a conjugate relationship to the exit pupil of the optical unit 42. Namely, the reflection section 44 relays the exit pupil of the optical unit 42 by re-forming the exit pupil at the reflection side, i.e. in the direction toward the observer OP.

As an example of the reflection member 48, in the present exemplary embodiment an optical image forming element 48A is employed to form an image of equivalent magnification by reflection plural times using plural reflection surfaces.

For example, the optical image forming element 48A is equipped with plural reflection members configured by plural reflection surfaces in stacked layers, with light incident to one stacked-layer end face being reflected by the reflection surfaces and emitted from the other stacked-layer end face. The plural reflection members are arranged such that the reflection surface of one reflection member and the reflection surface of another reflection member are oriented to face in intersecting directions, and such that the light emitted from a stacked-layer end face of one reflection member is incident to a stacked-layer end face of the other reflection member.

Namely, the incident light incident on the optical image forming element 48A is reflected by a first reflection surface, the reflected light is then reflected by a second reflection surface and then emitted from the optical image forming element 48A. The first reflection surface and the second reflection surface are arranged in the optical image forming element 48A such that the reflection surfaces thereof face in intersecting (orthogonal) directions. Thus, when the first reflection surface and the second reflection surface are orthogonally arranged in plan view, the incident light to the optical image forming element 48A and the light emitted from the optical image forming element 48A are parallel when the optical image forming element 48A is viewed in plan view. Thus, plural light points that are actual points on the incident side of the optical image forming element 48A are converged on the exit side of the optical image forming element 48A and formed as an image of virtual points. Thus, in the present exemplary embodiment, the reflection section 44 re-forms the exit pupil at positions having a conjugate relationship to the exit pupil of the optical unit 42.

Note that the optical image forming element 48A can be treated as being a recursive element, or more precisely as being a recursive pass-through element. Recursive reflection is reflecting light in an opposite direction to the direction of light incident to the element using plural orthogonal reflection surfaces. However, the optical image forming element 48A has the property of letting incident light pass through to a face on the opposite side to the incident face, and to emit the light with changed direction when doing so, replicating light beams with plane symmetry with respect to a flat plane orthogonal to a normal to the optical image forming element. In this action, when the optical image forming element performs spatial replication, the progression direction of light beams is not changed in relation to the perpendicular direction of the optical image forming element 48A, and corresponds to a recursive action, and so the optical image forming element 48A can be thought of as being a recursive pass-through element. One example of the recursive element is a technique described in U.S. Patent Publication No. 2018/0284470, the disclosure of which is incorporated herein by reference in its entirety.

Another example of the optical image forming element 48A is a light control panel including plural intersecting reflection surfaces as a unit optical system, with plural of these unit optical systems arrayed along the directions of a flat plane intersecting with the plural reflection surfaces. More specifically, a light control panel is formed by arraying plural unit optical systems configured from two substantially mutually orthogonal mirror faces that are substantially perpendicular to a prescribed flat plane, such as for example, two-face corner reflectors.

FIG. 5 illustrates an example of optical paths in the display device 40.

As illustrated in FIG. 5, each of the pixels of the imaging image Im of the object OB formed by the display section 30 emits a parallel light beam from the exit pupil Exp of the optical unit 42, and a pupil is re-formed by the exit pupil being replicated and formed by the optical image forming element 48A. In the display device 40, the exit pupil Exp of the optical unit 42 forms an exit pupil Exp at a position on the outermost surface on the light exit side of the optical unit 42, forming eye points Ept. The eye points Ept are ranges where light emitted from the optical unit 42 is visible over all angles of view. In the example illustrated in FIG. 5, ranges in the optical axis direction up to a distance Lz from the exit pupil Exp are the eye points Ept.

The pupil is re-formed by replicating with the optical image forming element 48A and forming the conjugate relationship exit pupil Exp. Thus, an eye point Ept1 is formed conjugate to an eye point Ept on the light exit side of the optical unit 42, and an eye point Ept2 is also formed further along the light progression direction. This results in eye points where the observer OP is able to observe at both the eye point Ept1 and the eye point Ept2, enabling eye points to be formed over a double range, and enabling the range over which the position of the eyes of the observer OP, namely the position of the head of the observer OP, is able to move to be expanded to the double range. The permissible range defined for the position of the head of the observer OP can thereby be expanded, enabling the degrees of freedom for setting the position of the head of the observer OP to be raised.

Note that in the example illustrated in FIG. 5, the optical paths of the display device 40 are illustrated for a flat plane containing the optical axis CL, and a viewable range covering all angles of light emitted from the optical unit 42 is illustrated by the eye point Ept. However, the light emitted from the optical unit 42 is composed of light beams having rotational symmetry about an axis of the optical axis CL. Thus, the eye point Ept can be thought of as being an eye box of a substantially conical shaped region with an axis along the optical axis CL.

Figure 6:
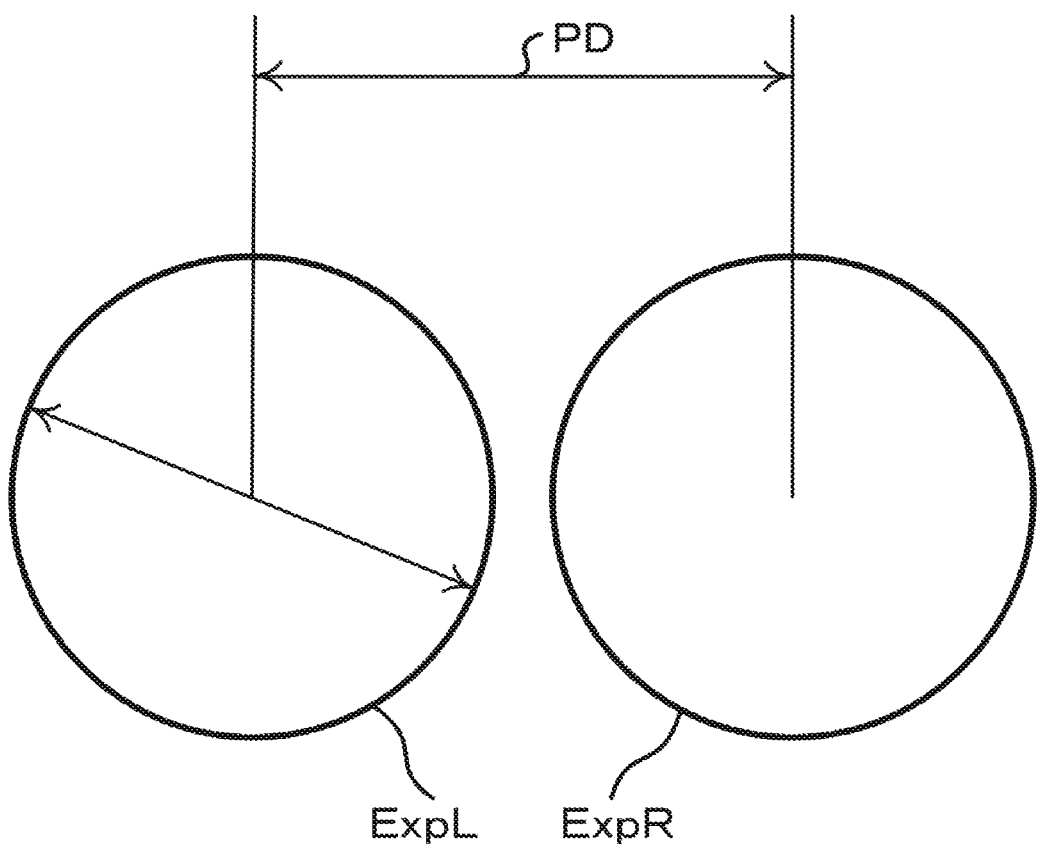
FIG. 6 is a sketch illustrating an example of exit pupils in a display device included in a fundus imaging system according to an exemplary embodiment.

FIG. 6 illustrates an example of the exit pupils Exp in the display device 40 according to the present exemplary embodiment.

As illustrated in FIG. 6, the exit pupils Exp of the display device 40 are formed by a right-eye exit pupil ExpR and a left-eye exit pupil ExpL.

Moreover, the present exemplary embodiment is configured such that the positions of the exit pupils Exp are positioned on the outermost surface on the light exit side of the optical unit 42. This accordingly enables the exit pupils of the optical unit 42 to be formed with a size corresponding to the lens diameter of the optical unit 42, enabling the diameters of the right-eye exit pupil ExpR and the left-eye exit pupil ExpL to be expanded to a size corresponding to the lens diameter of the optical unit 42. By positioning each of the eyes of the observer OP inside the exit pupil of the right-eye exit pupil ExpR and the left-eye exit pupil ExpL respectively, the observer OP is able to visually confirm an imaging image ImR for the right-eye of the observer OP and an imaging image ImL for the left-eye of the observer OP. The ophthalmic imaging system 10 of the present exemplary embodiment accordingly does not need a mechanism to adjust the pupil distance PD such as is installed in a binocular view microscope of related art.

The size, namely the diameter, of the right-eye exit pupil ExpR and the left-eye exit pupil ExpL is limited by the lens diameter of the optical unit 42. However, there are cases in which there is a demand for the size of the exit pupils Exp to be expanded to give the observer OP a larger range of visibility. In such cases, the lens diameter of the optical unit 42 can be made larger than the pupil distance PD, such that portions of the optical unit 42 overlap with each other.

Figure 7:
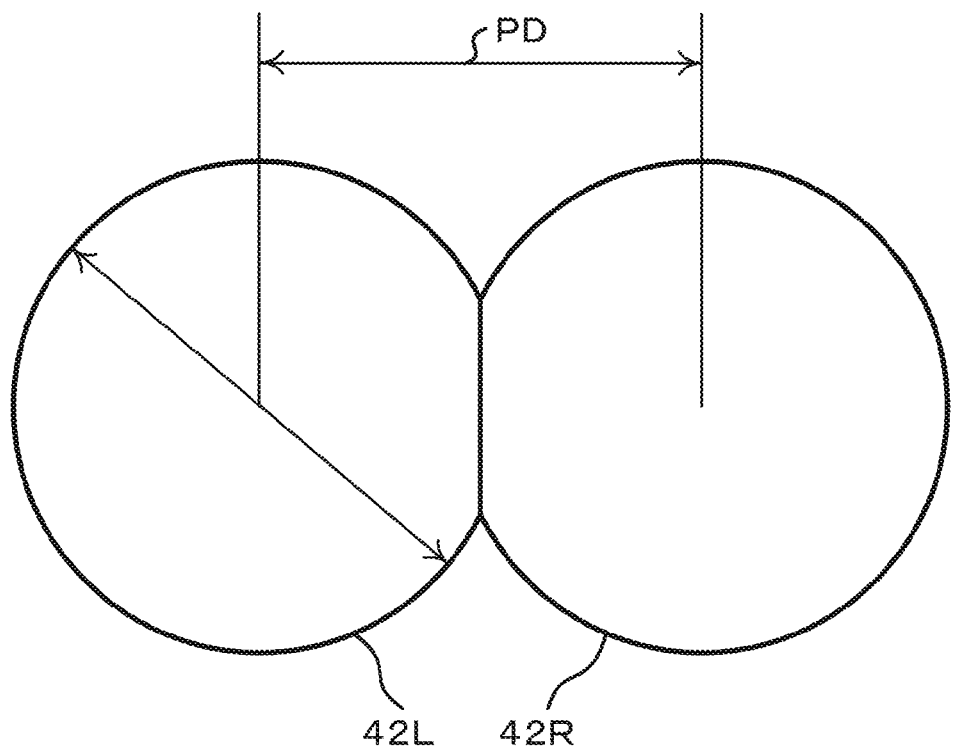
FIG. 7 is a sketch illustrating an example of an optical unit included in an ophthalmic imaging system according to an exemplary embodiment.

FIG. 7 illustrates an example of a configuration of an optical unit 42 in which the lens diameter is larger than the pupil distance PD.

In cases in which the lens diameter of the optical unit 42 is larger than the pupil distance PD, the right-eye optical unit 42R and the left-eye optical unit 42L interfere with each other, and so the optical unit 42 may be formed by removing an interfering portion of at least one of the right-eye optical unit 42R or the left-eye optical unit 42L. The example illustrated in FIG. 7 is of a case in which portions of the optical unit 42 have been removed uniformly from the right-eye optical unit 42R and the left-eye optical unit 42L. Adopting such a configuration enables the separation between the optical axis of the right-eye optical unit 42R and the optical axis of the left-eye optical unit 42L to be maintained at the pre-set pupil distance PD, and enables larger exit pupils Exp to be formed than in cases in which the optical unit 42 is formed with a diameter corresponding to the pupil distance PD.

There are cases in which the observer OP may wish to change their line of gaze when viewing the imaging image Im of the object OB. Thus, the ophthalmic imaging system 10 according to the present exemplary embodiment can be configured such that the optical axis of the imaging image Im of the object OB being displayed toward the observer OP is adjustable.

Figure 8:
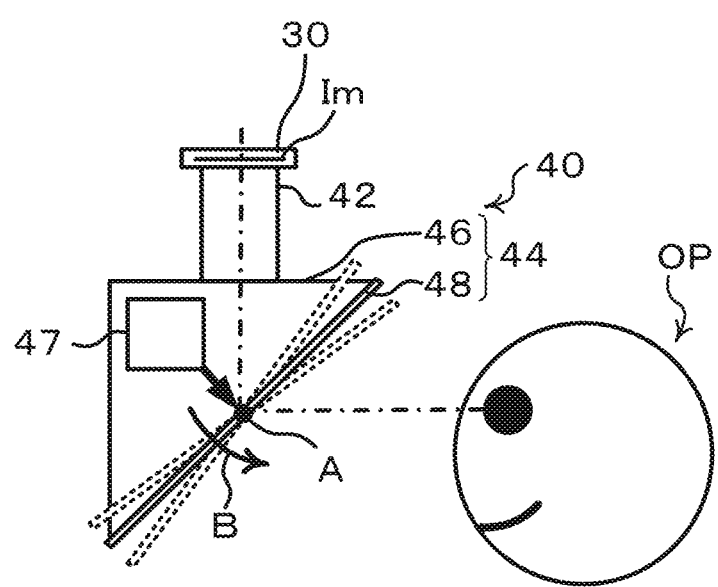
FIG. 8 is a block diagram illustrating an example of a configuration of a display device configured so as to be able to adjust an optical axis of an imaged image, according to an exemplary embodiment.

FIG. 8 illustrates an example of a configuration of the display device 40 configured such that the optical axis of the imaging image Im is adjustable.

As illustrated in FIG. 8, the reflection member 48 is formed so as to be rotatable about an axis A along a direction intersecting with the emitting optical axis of the optical unit 42. The reflection section 44 is equipped with a rotation drive section 47 to rotationally drive the reflection member 48. For example, in cases in which the optical axis is set along a horizontal direction, rotating the reflection member 48 by an angle γ in a counterclockwise direction (direction indicated by arrow B in FIG. 8) under driving from the rotation drive section 47 results in the optical axis being rotated by an angle φ in the counterclockwise direction. The observer OP is thereby able to change the direction of gaze when viewing the imaging image Im downwards from the horizontal direction. Rotating the reflection member 48 by an angle φ in a clockwise direction (the opposite direction to arrow B in FIG. 8) under driving from the rotation drive section 47 results in the optical axis being rotated by an angle 2φ in the clockwise direction. The observer OP is thereby able to change the direction of gaze when viewing the imaging image Im upwards from the horizontal direction.

Note that although, in the example illustrated in FIG. 8, the reflection member 48 is formed so as to be rotatable about axis A, the position of axis A is not limited thereto, and as long as the reflection member 48 can be rotated, the position of the axis A may be any position on the reflection member 48, and may also be formed outside the reflection member 48.

Moreover, when the observer OP has farsightedness or myopia, sometimes it is difficult to align the focal point to the imaging image Im of the object OB viewed with the ophthalmic imaging system 10, namely, sometimes the imaging image Im is blurred when viewed. Thus, the ophthalmic imaging system 10 according to the present exemplary embodiment may be equipped with a diopter adjustment mechanism to adjust diopters to match the eyes of the observer OP.

FIG. 9 schematically illustrates an example of a diopter adjustment mechanism to adjust diopters to match the eyes of the observer OP. The diopter adjustment mechanism may be formed such that parallel light emitted toward the observer OP is emitted as divergent light or converging light.

As illustrated in FIG. 9, in order to change parallel light emitted toward the observer OP so as to be emitted as divergent light or converging light, the position of at least one out of the display section 30 forming the imaging image Im or the optical unit 42 is displaced along the optical axis direction. Namely, a display position adjustment section 32 to change the position of the display section 30 forming the imaging image Im and a lens position adjustment section 43 to change the position of the optical unit 42 are provided. Note that changing the position of the optical unit 42 also changes the position of the exit pupils, and so a configuration in which the position of the display section 30 is changed is preferably adopted.

The example illustrated in FIG. 9 illustrates a case in which the position of the display section 30 has been moved by the display position adjustment section 32 to make the display section 30 further away from the optical unit 42 by a distance L1. Parallel light toward the observer OP is thereby emitted as divergent light, extending the focal position by a distance L2. This enables the diopter adjustment for myopia. Bringing the display section 30 closer to the optical unit 42 enables the diopter adjustment for farsightedness.

The reflection member 48 is an element that lets light pass through, but in cases in which the optical image forming element 48A is employed therein, sometimes due to the structure of the optical image forming element 48A, namely, due to the presence of the plural reflection surfaces, light scattered by these reflection surfaces is, for example, seen by the observer OP, and the focal point of viewing by the observer OP falls on the optical image forming element 48A. Thus, the ophthalmic imaging system 10 according to the present exemplary embodiment may be equipped with a suppression mechanism to suppress the focal point of viewing by the observer OP from falling on the optical image forming element 48A. In the present exemplary embodiment, as an example of a suppression mechanism, the focal point of viewing by the observer OP is suppressed from falling on the optical image forming element 48A by using oscillation achieved by oscillating the optical image forming element 48A. Light passing through the light-passing reflection member 48 is light with a progression state arising from at least one action out of light being reflected by a reflection surface, light passing through, light passing through a transmission medium, or light proceeding with a deflected optical path due to refraction.

Figure 10A:
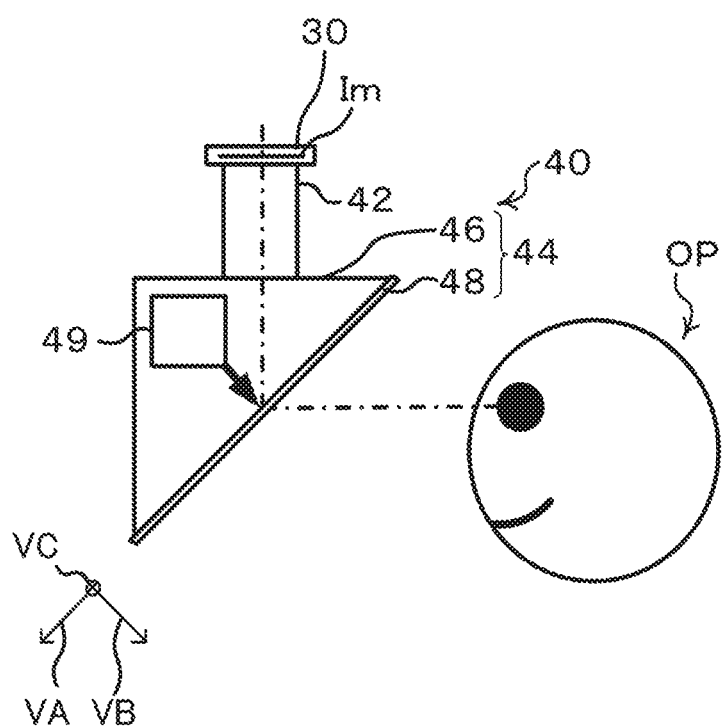
FIGS. 10A and 10B are schematic diagrams illustrating an example of a suppression mechanism to suppress a focal point of a gaze falling on an optical image forming element in an ophthalmic imaging system according to an exemplary embodiment.
Figure 10B:
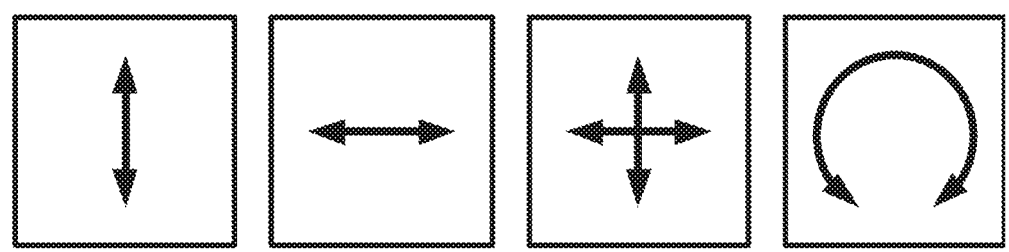

FIGS. 10A and 10B schematically illustrate an example of a suppression mechanism 49. FIG. 10A illustrates an example of a configuration of the suppression mechanism 49. FIG. 10B illustrates an example of oscillation directions of the optical image forming element 48A by the suppression mechanism 49. The suppression mechanism oscillates the optical image forming element 48A periodically so that the optical image forming element 48A does not remain in the same position.

As illustrated in FIG. 10A, the suppression mechanism 49 is a drive section for driving so as to move the optical image forming element 48A in at least one direction from out of a direction (arrow VB direction) normal to the surface of the optical image forming element 48A, different directions intersecting with the normal direction (arrow VA and VC directions), or a direction of rotation thereabout. The suppression mechanism 49 preferably drives the optical image forming element 48A so as to maintain the exit angle of the optical image forming element 48A. Namely, the suppression mechanism 49 performs at least one type of driving on the optical image forming element 48A out of oscillation or rotation in at least one of the directions illustrated in FIG. 10B, while the optical image forming element 48A maintains the exit angle of the reflected light. The optical image forming element 48A is preferably actuated periodically in consideration of the viewing periodicity when the observer OP is pinpointing an object. For example, the actuation periodicity is preferably set to a periodicity of not less than 30 Hz. Actuation of the optical image forming element 48A by the suppression mechanism 49 suppresses the focal point viewed by the observer OP from falling on the optical image forming element 48A. Note that the suppression mechanism 49 is a device that performs at least one type of driving from out of oscillation or rotation; however, an oscillation device to oscillate by performing at least one type of driving from out of straight line driving, curved arc driving, or rotational driving may be employed therefor.

Note that although, in the present exemplary embodiment, an example of the ophthalmic imaging system 10 has been described in which the reflection member 48 that can be treated as a recursive pass-through element is employed as an example of the optical image forming element 48A, the reflection member 48 is not limited by the optical image forming element 48A. For example, a recursive element that includes functionality that does not change the progression direction of light beams when replicating in space may also be employed therefor.

First Modified Example

FIG. 11 illustrates a first modified example related to the display device 40 of the ophthalmic imaging system 10.

As illustrated in FIG. 11, in the first modified example, the reflection section 44 included in the display device 40 includes a case 46, a recursive reflection member 47A such as a reflection array in which plural corner cubes equipped with plural orthogonal reflection surfaces are arrayed in a two-dimensional flat plane shape, and a half mirror 48B. The display device 40 of the first modified example reflects light emitted from the optical unit 42 using the half mirror 48B. The light reflected by the half mirror 48B is emitted toward the recursive reflection member 47A, is recursively reflected thereat, passes through the half mirror 48B, and is emitted toward the observer OP.

Second Modified Example

Figure 12:
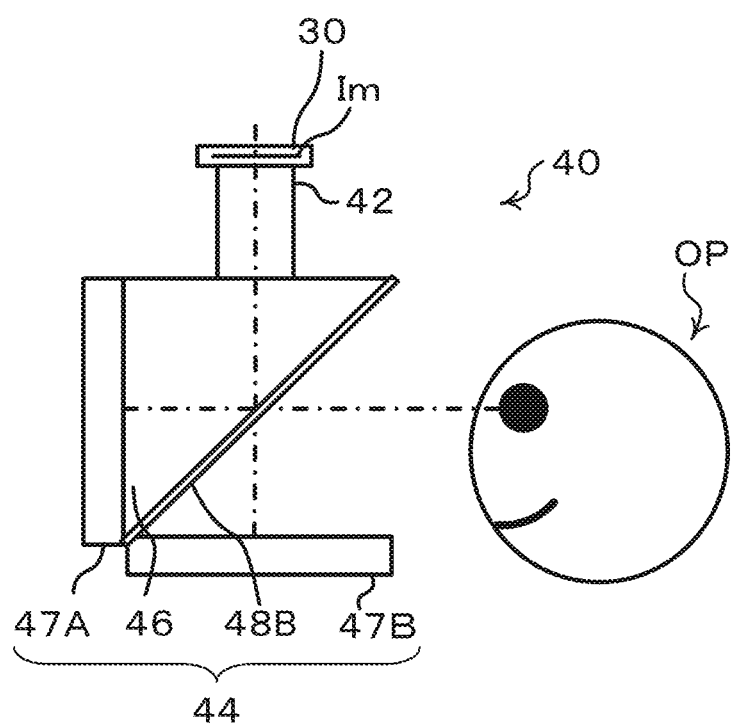
FIG. 12 is a block diagram illustrating a second modified example related to a display device in an ophthalmic imaging system according to an exemplary embodiment.

FIG. 12 illustrates a second modified example related to the display device 40 of the ophthalmic imaging system 10.

As illustrated in FIG. 12, in the second modified example, a reflection section 44 included in the display device 40 includes a case 46, recursive reflection members 47A, 47B such as reflection arrays in which plural corner cubes equipped with plural orthogonal reflection surfaces are arrayed in a two-dimensional flat plane shape, and a half mirror 48B. In the display device 40 of the second modified example, light emitted from the optical unit 42 is reflected by the half mirror 48B. The light reflected by the half mirror 48B is emitted toward the recursive reflection member 47A, is recursively reflected thereat, passes through the half mirror 48B, and is emitted toward the observer OP. Moreover, light that has passed through the half mirror 48B from out of the light emitted from the optical unit 42 is emitted toward the recursive reflection member 47B, is recursively reflected thereat, is reflected by the half mirror 48B, and is emitted toward the observer OP.

The second modified example is able to utilize the light that has passed through the half mirror 48B, and this thereby enables the light intensity of the imaging image Im viewed by the observer OP to be increased in comparison to in the first modified example.

Third Modified Example

Figure 13:
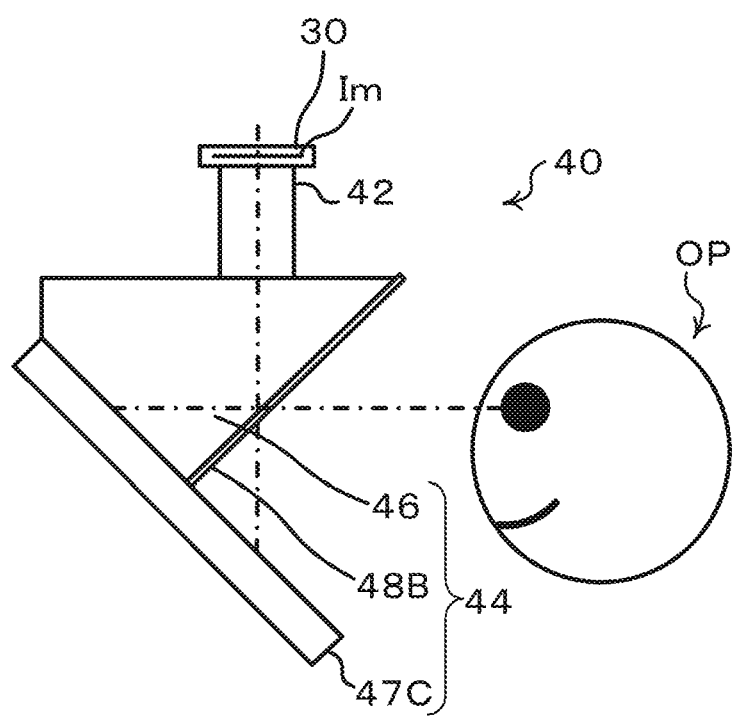
FIG. 13 is a block diagram illustrating a third modified example related to a display device in an ophthalmic imaging system according to an exemplary embodiment.

FIG. 13 illustrates a third modified example related to the display device 40 of the ophthalmic imaging system 10.

As illustrated in FIG. 13, in the third modified example, the reflection section 44 included in the display device 40 includes a case 46, recursive reflection member 47C such as a reflection array in which plural corner cubes equipped with plural orthogonal reflection surfaces are arrayed in a two-dimensional flat plane shape, and a half mirror 48B. In the display device 40 of the third modified example, the light emitted from the optical unit 42 is reflected by the half mirror 48B. The light reflected by the half mirror 48B is emitted toward the recursive reflection member 47C, is recursively reflected thereat, passes through the half mirror 48B, and is emitted toward the observer OP. Moreover, the light that has passed through the half mirror 48B from out of the light emitted from the optical unit 42 is emitted toward the recursive reflection member 47C, is recursively reflected thereat, is reflected by the half mirror 48B, and is emitted toward the observer OP.

Thus, in the third modified example, due to the reflected light and the light that has passed through the half mirror 48B both being recursively reflected by the common recursive reflection member 47C, a display device can be formed in which the number of elements of the recursive reflection member is reduced in comparison to the second modified example.

Fourth Modified Example

Figure 14:
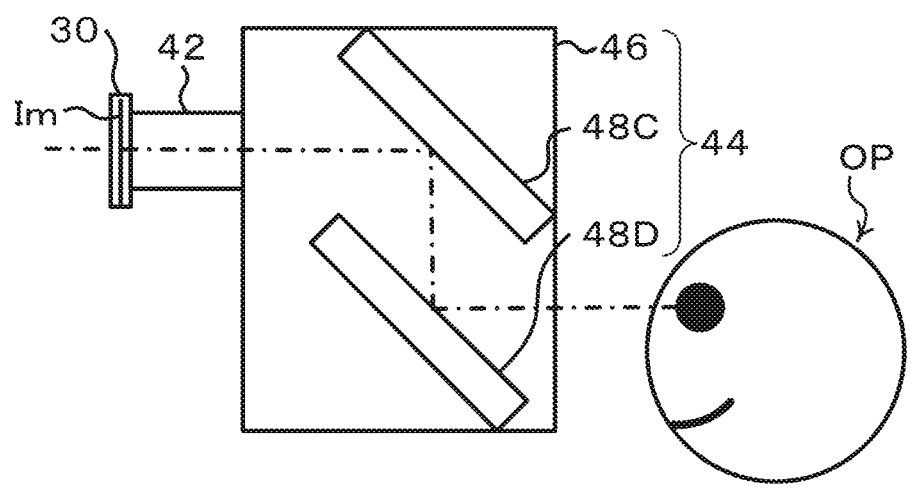
FIG. 14 is a block diagram illustrating a fourth modified example related to a display device in an ophthalmic imaging system according to an exemplary embodiment.

FIG. 14 illustrates a fourth modified example related to the display device 40 of the ophthalmic imaging system 10.

As illustrated in FIG. 14, in the fourth modified example, a reflection section 44 included in the display device 40 includes a case 46, and prism sheet mirrors 48C, 48D with two-face corner reflectors arrayed along one direction. In the display device 40 of the fourth modified example, the light emitted from the optical unit 42 is reflected sequentially by the prism sheet mirrors 48C, 48D. The light emitted from the optical unit 42 is reflected sequentially by the prism sheet mirrors 48C, 48D, and emitted toward the observer OP. The configuration in which the light emitted from the optical unit 42 is reflected sequentially by the prism sheet mirrors 48C, 48D is adopted so that a shape distorted by reflection by one prism sheet mirror is corrected by the second prism sheet mirror.

Although, in the fourth modified example, a configuration is adopted in which a shape distorted by being reflected by one prism sheet mirror is corrected by the second prism sheet mirror, the reflection section 44 included in the display device 40 of the fourth modified example may be configured by a single prism sheet mirror in cases in which some distortion by one prism sheet mirror is permitted.

Moreover, although the first modified example to the fourth modified example have been described in relation to the display device 40 of the ophthalmic imaging system 10, obviously similar advantageous effects are exhibited by each of the first modified example to the fourth modified example to cases in which the reflection member 48 employs the optical image forming element 48A.

The ophthalmic imaging system 10 according to the present exemplary embodiment includes the display section 30 such as a display attached to an upper portion of the display device 40, and is configured to display the imaging image Im formed by the display section 30 toward the observer OP through the optical unit 42 and the reflection member 48 (see FIG. 1 and FIG. 2). However, the image display system according to technology disclosed herein is not limited to a system in which the display section 30 is attached to an upper portion of the display device 40. For example, the display section 30 may be attached to a lower portion of the display device 40, and a configuration may be adopted to display the imaging image Im formed by the display section 30 toward the observer OP through the optical unit 42 and the reflection member 48 with an optical axis running from bottom to top in the display device 40. Namely, the position where the display section 30 is attached to the display device 40 may be any position on the display device 40, and the optical axis direction toward the display device 40 may be configured so as to face in any direction with respect to the display device 40.

Note that although, in the present exemplary embodiment, an ophthalmic imaging system applied with an ophthalmic imaging device has been described as an example of an image display system according to technology disclosed herein, the image display system according to technology disclosed herein is not limited to an ophthalmic imaging system applied with an ophthalmic imaging device. Namely, in the technology disclosed herein, an image display device according to technology disclosed herein is applicable to any device for displaying images, and an image display system according to technology disclosed herein is applicable to any system equipped with a device for displaying images. Explanation next follows regarding examples of image display devices to which the technology disclosed herein is applicable, and to application examples of image display systems equipped with such image display devices.

First Application Example

A first application example is an example of application to a display device of an observation system for observing distant objects using an optical instrument such as binoculars, a periscope, or the like. By applying the image display device or the image display system according to the technology disclosed herein to an observation system to observe distant objects, the observer OP is able to observe distant objects in a non-contact state with respect to the display device 40, suppressing the observer OP from feeling unsettled by contact that occurs. Moreover, the apparent size of an image being viewed with the optical unit 42 does not change, and so the head of the observer OP is able to move within the eye points (eye boxes). There is accordingly a larger permitted range of postures of the observer OP compared to the posture when the head of the observer OP contacts an optical instrument such as binoculars, a periscope, or the like.

Second Application Example

A second application example is an example of application to a display device of a gaming system employed in a game machine for a gamer to play while viewing an image related to the game. By applying the image display device or the image display system according to the technology disclosed herein to a gaming system, the gamer is able to view the image related to the game in a non-contact state with respect to the display device 40, suppressing the gamer from feeling unsettled by contact that occurs during gaming. Moreover, due to the apparent size of the image viewed with the optical unit 42 not changing, the head of the gamer is able to move within the eye points (eye boxes), resulting in a larger permitted range for the posture of the gamer in comparison to the posture when the head of the gamer contacts a display device. Moreover, an image displayed on a gaming system applied with the image display device or the image display system according to the technology disclosed herein is only viewable within the eye points. Viewing from outside the eye points is accordingly suppressed, and, for example, in cases in which there are plural gaming systems provided in close proximity, viewing of the display image by another gamer next to the actual gamer is suppressed. This thereby suppresses game interference to another gamer due to an image not relevant to the adjacent gaming system being viewable.

Third Application Example

A third application example is an example of application to a display device of an audiovisual system employing an audiovisual device installed in an audiovisual room or the like to individually present audiovisual information including a pre-prepared image to an audiovisual consumer. By applying the image display device or the image display system according to the technology disclosed herein to such an audiovisual system, the audiovisual consumer can view the image in a non-contact state with respect to the display device 40 and is suppressed from feeling unsettled by contact occurring with the audiovisual device. Moreover, due to the apparent size of the image viewed with the optical unit 42 not changing, the head of the audiovisual consumer is able to move within the eye points, resulting in a larger permitted range for the posture of the audiovisual consumer in comparison to the posture when the head of the audiovisual consumer contacts the audiovisual device. Furthermore, the image being displayed on the audiovisual system applied with the image display device or image display system according to the technology disclosed herein is only viewable within the eye points. Viewing from outside the eye points is accordingly suppressed, and, for example, in cases in which application is made to an audiovisual system provided with plural display devices, individual images can be displayed to each of the audiovisual consumers with suppressed viewing by other audiovisual consumers, with the expectation of improved simultaneous presentation performance of plural audiovisual information.

Fourth Application Example

A fourth application example is an example of application to an image presentation system display device employing an image presentation device to present images that has been installed in an individual space of a person in a net café, recreation room, or the like. By applying the image display device or the image display system according to the technology disclosed herein to such an image presentation system, the person is able to view images in a non-contact state with respect to the display device 40, and is suppressed from feeling unsettled by contact occurring with the image presentation device. Moreover, due to the apparent size of the image viewed with the optical unit 42 not changing, the head of the person is able to move within the eye points, resulting in a larger permitted range for the posture of the person in comparison to the posture when the head of the person contacts the image presentation device.

Fifth Application Example

A fifth application example is an example of application to a display device of a design system for an operator to design products using a computer such as in computer aided design (CAD) or the like. By applying the image display device or the image display system according to the technology disclosed herein to such a design system, the operator is able to view images during design in a non-contact state with respect to the display device 40, and is suppressed from feeling unsettled by contact occurring with the display device. Moreover, due to the apparent size of the image viewed with the optical unit 42 not changing, the head of the operator is able to move within the eye points, resulting in a larger permitted range for the posture of the operator in comparison to the posture when the head of the operator contacts the image display device. Furthermore, images displayed in the design system applied with the image display device or the image display system according to the technology disclosed herein are only viewable within the eye points. Viewing from outside the eye points is accordingly suppressed, enabling individual images to be displayed to the operator alone, and suppressing images from being viewed by other persons during design.

Sixth Application Example

A sixth application example is an example of application to a display device of a cash telling system employing an automated teller machine (ATM) to perform the exchange of cash information such as information regarding a user paying-out/paying-in cash, balance verification, or the like. By applying the image display device or the image display system according to the technology disclosed herein to such a cash telling system, the user is able to check images related to the exchange of cash information in a non-contact state with respect to the display device 40, and is suppressed from feeling unsettled by contact occurring with the ATM. Moreover, due to the apparent size of the image viewed with the optical unit 42 not changing, the head of the user is able to move within the eye points, resulting in a larger permitted range for the posture of the user in comparison to the posture when the head of the payee/dispensee contacts the ATM. Furthermore, images displayed in the cash telling system applied with the image display device or the image display system according to the technology disclosed herein are only viewable when inspected within the eye points. Viewing from outside the eye points is accordingly suppressed, enabling viewing of the display images by someone other than the user to be suppressed, with the expectation of improved security performance in comparison to ordinary image display.

Seventh Application Example

A seventh application example is an example of application to a display device of an application system to perform various types of application and verification by employing an application device for an applicant to perform various types of application based on personal information at a public organization such as a government office. Due to applying the image display device or the image display system according to the technology disclosed herein to such an application system, the applicant can view images related to the various types of application based on personal information in a non-contact state with respect to the display device 40, suppressing an unsettling feeling due to contact with application device from occurring. Moreover, due to the apparent size of the image viewed with the optical unit 42 not changing, the head of the applicant is able to move within the eye points, resulting in a larger permitted range for the posture of the applicant in comparison to the posture when the head of the applicant contacts the application device. Furthermore, images related to the various types of application performed based on the personal information are only viewable when inspected within the eye points. Viewing from outside the eye points is accordingly suppressed, enabling viewing of the display image by someone other than the applicant to be suppressed, with the expectation of improved security performance in comparison to ordinary image display.

Eighth Application Example

An eighth application example is an example of application to a display device of a booking/verification system employing a booking/verification device for a booker to book or verify a seat on transportation such as a boat, airliner, train, or the like, a seat in a cinema, theater, or the like, or a seat in an eatery such as a restaurant or the like. By applying the image display device or the image display system according to the technology disclosed herein to such a booking/verification system, the booker is able to view images to book or verify a seat in a non-contact state with respect to the display device 40, and is suppressed from feeling unsettled by contact occurring with the booking/verification device. Due to the apparent size of the image viewed with the optical unit 42 not changing, the head of the booker is able to move within the eye points, resulting in a larger permitted range for the posture of the booker in comparison to the posture when the head of the booker contacts the booking/verification device. Furthermore, images to book or verify a seat are only viewable when inspected within the eye points. Viewing from outside the eye points is accordingly suppressed, enabling viewing of the display image by someone other than the booker to be suppressed, with the expectation of improved security performance in comparison to ordinary image display.

Ninth Application Example

A ninth application example is an example of application to a display device of an image viewing system employing a viewing device for a viewer to view images in a seat on various transportation such as a boat, airline, train or the like. Due to applying the image display device or the image display system according to the technology disclosed herein to such an image viewing system, the viewer is able to view images in their seat in a non-contact state with respect to the display device 40, and is suppressed from feeling unsettled by contact occurring with the image viewing device. Moreover, due to the apparent size of the image viewed with the optical unit 42 not changing, the head of the viewer is able to move within the eye points, resulting in a larger permitted range for the posture of the viewer in comparison to the posture when the head of the viewer contacts the image viewing device. Furthermore, images to be viewed by the viewer are only viewable within the eye points. Viewing from outside the eye points is accordingly suppressed, namely, viewing of the display image by someone other than the viewer is suppressed, with the expectation of improved security performance in comparison to ordinary image display. Furthermore, images displayed with the image viewing system applied with the image display device or image display system according to technology disclosed herein are only viewable within the eye points, and are suppressed from being viewed by someone else. This enables individual images to be displayed to each of the viewers alone, suppressing viewing by someone else and having the expectation of improved exclusivity performance of image viewing in comparison to ordinary image display.

Moreover, the image display device of the present exemplary embodiment is equipped with the optical unit 42 and the reflection section 44. The optical unit 42 has a focal length, and is formed such that an imaged image of an object imaged by the imaging section 20 is set so as to be at the position of the focal point on the light incident side, and such that a position of an exit pupil is positioned at or beyond an outermost surface on the light exit side. The reflection section 44 is formed to reflect light emitted from the optical unit 42 and to form an exit pupil at a position on the reflection side having a conjugate relationship to the exit pupil.

Another a aspect of technology disclosed herein is an image display system including an imaging section to image an object, and the image display device equipped with a display section to display an image of the object imaged by the imaging section.

Note that although exemplary embodiments related to the technology disclosed herein have been described, the scope of technology disclosed herein is not limited to the scope of the above exemplary embodiments. Various modifications and improvements can be made to the exemplary embodiments described above without departing from the scope of the gist of the technology disclosed herein, and these modifications and improvements are included within the scope of the technology disclosed herein. Moreover, all publications, patent applications and technical standards mentioned in the present specification are incorporated by reference in the present specification to the same extent as if each individual publication, patent application, or technical standard was specifically and individually indicated to be incorporated by reference.

EXPLANATION OF REFERENCE NUMERALS 10 ophthalmic imaging system
20 imaging section
22 microscope
24 camera
26 camera controller
30 display section
40 display device
42 optical unit
44 reflection section
46 case
48 reflection member
Ept eye point
Exp exit pupil
Im imaged image
OB object
OP observer

The invention claimed is:

1. An image display device comprising:
an optical unit that has a focal point on an incident side of light at a position where an image of an object is set, and that is configured to form an exit pupil; and
an optical element configured to reflect or pass light emitted from the optical unit and relay the exit pupil to a position having a conjugate relationship to the exit pupil, wherein the optical element forms a first eye point with a conjugate relationship to an eye point on a light exit side of the optical unit, and forms a second eye point further to a progression direction side of the light than a position of the first eye point.

2. The image display device of claim 1, wherein light emitted from the optical unit is afocal.

3. The image display device of claim 1, wherein light emitted from the optical unit is parallel light.

4. The image display device of claim 1, wherein the optical element is a common member for the left eye and for the right eye.

5. The image display device of claim 1:
wherein the optical unit independently forms the exit pupil for use by a left eye of an observer and the exit pupil for use by a right eye of the observer.

6. The image display device of claim 1, wherein:
the optical element is disposed at a position distanced away from an observer; and
the exit pupil is relayed to an observation position between the optical element and the observer.

7. The image display device of claim 1, wherein:
the optical unit forms the exit pupil at a position at or beyond a lens nearest to the optical element.

8. The image display device of claim 1, wherein:
the optical unit forms the exit pupil at a position at or beyond an outermost surface on an exit side of the light.

9. The image display device of claim 1, wherein:
the image includes a left-eye image and a right-eye image.

10. An image display device comprising:
an optical unit that has a focal point on an incident side of light at a position where an image of an object is set, and that is configured to form an exit pupil; and
an optical element configured to reflect or pass light emitted from the optical unit and relay the exit pupil to a position having a conjugate relationship to the exit pupil, wherein:
the optical unit includes a first surface onto which light is incident formed by a first refraction surface having a convex face on an incident side of the light, and includes a last surface from which the light is emitted formed by a second refraction surface having a convex face toward an exit side of the light.

11. The image display device of claim 1, wherein the optical element includes a light control panel configured by a plurality of stacked-layer sections having a plurality of reflection surfaces stacked as layers such that the plurality of reflection surfaces mutually intersect.

12. The image display device of claim 1, wherein the optical element includes a light control panel configured by a plurality of intersecting reflection surfaces as a unit optical system, with a plurality of the unit optical systems arrayed in directions of a flat plane intersecting the plurality of reflection surfaces.

13. The image display device according to claim 11, wherein the optical element includes a drive section to perform at least one of oscillation or rotation in a predetermined direction with respect to the light control panel while the light control panel maintains an emission angle of reflected light.

14. The image display device of claim 1, wherein the optical unit
forms a focal length not greater than 100 mm so as to satisfy the following conditional equation:

$$f \leq (D/2)/\sin \theta$$

wherein f is the focal length, D is a size of the image, and θ is a light illumination half angle of view of light with respect to an optical axis.

15. The image display device of claim 1, wherein the optical unit forms a focal length of not less than 25 mm so as to satisfy the following conditional equation:

$$f \geq S/\tan R$$

wherein f is the focal length, S is a size of pixels configuring the image, and R is an eye resolving power.

16. The image display device of claim 1, wherein the optical unit is formed including a plurality of optical units such that optical axes of the plurality of optical units are parallel.

17. The image display device according to claim 16, wherein the plurality of optical units are formed separated by a distance corresponding to a separation between two eyes of an observer observing an image formed by light reflected by the optical element.

18. An image display system comprising:
an imaging section to image an object; and
the image display device of claim 1.

19. The image display system of claim 18, wherein the imaging section and the image display device are independent of each other.

\* \* \* \* \*

UNITED STATES PATENT AND TRADEMARK OFFICE
CERTIFICATE OF CORRECTION

| | |
|---|---|
| PATENT NO. | : 11,786,118 B2 |
| APPLICATION NO. | : 16/823833 |
| DATED | : October 17, 2023 |
| INVENTOR(S) | : Tomohiro Kawasaki et al. |

It is certified that error appears in the above-identified patent and that said Letters Patent is hereby corrected as shown below:

In the Claims

Column 21, Line 59:
In Claim 5, delete "1:" and insert --1,--.

Signed and Sealed this
Nineteenth Day of December, 2023

Katherine Kelly Vidal
*Director of the United States Patent and Trademark Office*